US00PP09355P

United States Patent [19]

Henny

[11] Patent Number: Plant 9,355

[45] Date of Patent: Oct. 31, 1995

[54] ANTHURIUM PLANT '75-10'

[75] Inventor: Richard J. Henny, Tavares, Fla.

[73] Assignee: Florida Foundation Seed Producers, Greenwood, Fla.

[21] Appl. No.: 353,571

[22] Filed: Dec. 9, 1994

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Henderson & Sturm

[57] ABSTRACT

A new variety of Anthurium is provided. The inflorescences are composed of red spathes with a red-purple spadix carried on dark red-brown peduncles. The flowers are held slightly above the foliage with the leaves being dark green, shiny and often have light reddish-brown petioles. The plant canopy width is greater than the canopy height and the plant habit is freely branching, compact and upright.

1 Drawing Sheet

SUMMARY OF THE INVENTION

This invention relates to a new and distinct Anthurium cultivar which is outstanding because of its attractive inflorescences composed of red spathes with a red-purple spadix carried on dark red-brown peduncles. The flowers are held slightly above the foliage with the leaves being dark green, shiny and often have light reddish-brown petioles. The plant canopy width is greater than the canopy height and the plant habit is freely branching, compact and upright. This cultivar was primarily selected for those characteristics being so selected from a planting of Anthurium being grown near Apopka, Fla. in a cultivated area.

ORIGIN AND ASEXUAL REPRODUCTION

Asexual reproduction of this cultivar by division and/or tissue culture was directed by me, was used to increase the number of plants for evaluation and has demonstrated the stability of the combination of characteristics of the new cultivar from generation to generation.

It should be noted that the plant was initially selected where grown in or nera Apopka, Fla. and has since been reproduced by division and tissue culture with the characteristics stated, found to be maintained in successive generations.

The cultivar may further be described as having a number of distinctive characteristics which are enumerated in the succeeding specific description but broadly stated as comprising attractive inflorescences composed of red spathes with a red-purple spadix carried on dark red-brown peduncles. The flowers are held slightly above the foliage with the leaves being dark green, shiny and often have light reddish-brown petioles. The plant canopy width is greater than the canopy height and the plant habit is freely branching, compact and upright which makes this cultivar suitable for commercial distribution as a flowering pot plant.

I have chosen to identify this new cultivar as Anthurium '75-10'.

It is possible that other identification will be adopted in the trade, but the name selected will serve for the purposes hereof.

BRIEF DESCRIPTION OF THE PHOTOGRAPHS

The accompanying photographs show as nearly true as it is reasonably possible to make the same, in a color illustration of this character, typical specimens of the plant parts of the new variety. The plant of the new variety in FIG. 1 was approximately 12 months after planting 4–5 cm liner obtained from tissue culture. The plant of the new variety in FIG. 2 was approximately 24 months from a small division.

In the photographs:

FIG. 1 discloses the new variety;

FIG. 2 illustrates the inflorescences of the present invention.

DETAILED DESCRIPTION

Figure 2:
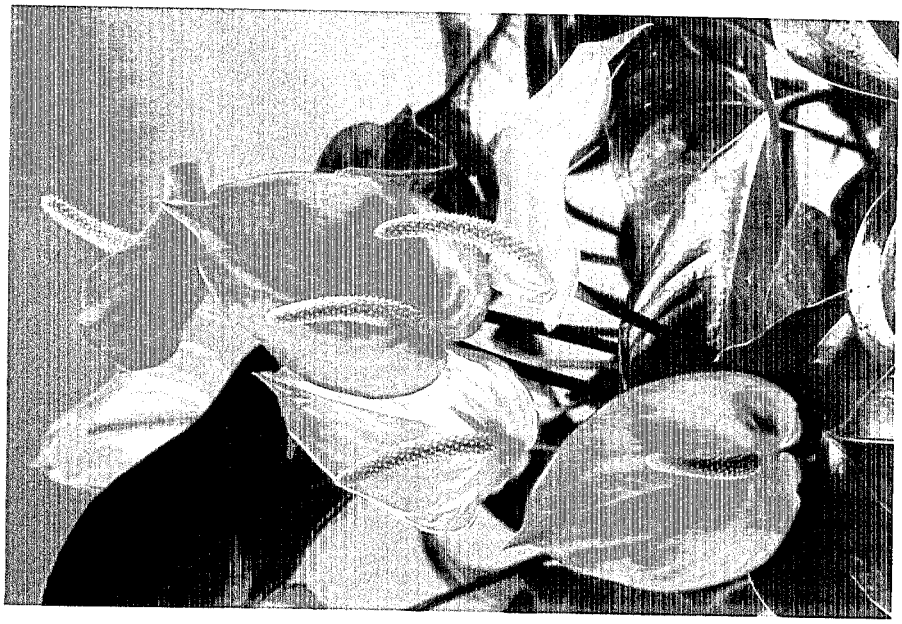
Figure 1:
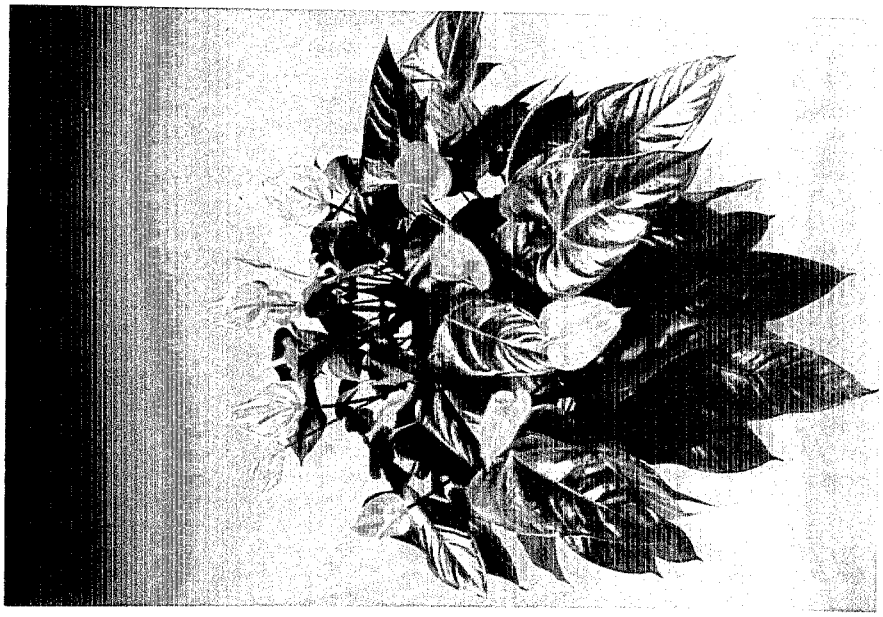

In order to more specifically identify the cultivar descriptive details are set forth hereinafter, along with related aspects of the plant which serve to distinguish the same all colors being noted as compared with The Royal Horticultural Society Colour Chart. The measurements and colors were recorded in from mature plants grown in the vicinity of Apopka, Fla.

Parentage:

*Seed parent.*—*Anthurium amnicola*×Anth. 'G-79'*= Anth. '3-1'.

*Pollen parent.*—Anthurium '3-1'×Anth. 'Lady Jane'= Anth. '75-10'. *Note: Anth. 'G-79'=Unidentified *Anth. andraeanum type.*

Propagation: Asexual reproduction either by tissue culture and division near Apopka, Fla.

Plant descriptions:

*Plant*—In a 15 cm pot after approximately 11 months of growth under appropriate conditions from a plantlet obtained from tissue culture, '75-10' will be at a mature size of approximately 25 to 30 cm to cm in height, and approximately 40 to 50 cm in width. All measurements are based on the above parameters.

*Foliage*—Form: The lamina is ovate with an acuminate tip and a cordate base with a sometimes decurrent blade. The midrib tends to curve slightly downward toward the tip of the leaf. The leaf margins tend to be slightly wavy over the length of the leaf. Size: Leaf blades of a mature plant will be approximately 18 cm to 22 cm in length and 10 cm to 13 cm in width. Petiole: The petiole is approximately 20 cm to 24 cm in height from the base of the petiole to the base of the leaf blade on the primary shoot. Secondary shoots are somewhat smaller depending on the age of the shoot. The petiole will be approximately 3.5 mm to 4.5 mm in diameter just below the geniculum. The petiole, just below the geniculum, will generally be straight. Petiole Petiole wings are approximately 3.5 cm to 4.5 cm in length wings: and approximately 4 mm to 6 mm in width at their midpoint. The tip of the petiole wings will be acute. There is approximately 20 cm to 27 cm between the top of the petiole wing and the base of the geniculum. Geniculum: The geniculum is approximately 2 cm to 2.5 cm in length, approximately 4 mm to 4.5 mm in diameter, and is straight or moderately curved. The color is 181A on the upper surface which may be exposed to direct light, and the color of the lower surface is 151A. There is no space between the top of the geniculum and the base of the leaf blade. The geniculum is prominent. Veins: Veins are sunken, with the leaf blade slightly convex between veins on the upper surface. The midrib protrudes from the upper surface of the leaf for approximately ⅔ of the length of the leaf. Well defined primary veins radiate out from the juncture of the petiole and the leaf. Primary veins stand out prominent on the lower leaf surface. There are approximately six primary lateral veins on the leaf. Color: Upper leaf surface: 147A. Lower leaf surface: 146B. Midrib, upper surface: 175A. Midrib, lower surface: 151B. Petiole, upper surface: 183B. Petiole, lower surface: 151B. Petiole wing: 146B.

*Inflorescence*—Immature: The spathe is tightly rolled around the spadix and emerges from the petiole sheath. The spathe is fully open approximately when the pedicel is fully elongated, approximately 20 cm to 28 cm above the soil surface. The color of the peduncle is 171B. Mature: Size: The fully expanded spathe is approximately 7 cm long and approximately 5 cm in width. Color: Newly opened: Upper surface: 47B. Lower surface: 48A. Faded: Upper surface: 39B. Lower surface: 38A. Position: The Inflorescence terminates a straight wiry peduncle and opens vertically above the leaves. Shape: The spathe is ovate with an obtuse or slightly cordate base and a cuspidate apex which is curved. It is slightly cupped when first open and is approximately 5 cm to 6.5 cm in height and approximately 3 cm to 3.5 cm in width. It is approximately 5 mm to 8 mm in depth. The spathe flattens and may develop somewhat wavy margins as it ages. Flowering Time: After apprxomately 9 months from a small 4–5 leaf cutting, an untreated plant may be 2–4 inflorescences present depending on the season. Smaller blossoms may occur on less mature growth. Once flowering is initiated, plants flower continually under normal production conditions. Spadix: Size: Approximately 2.5 cm to 4 cm in length and approximately 5 mm to 7 mm in width. Color: When the spathe unfurls, the spadix is 34A at the tip, blending to 53B. The spadix gradually changes to 48B prior to senescence. Stamens: Anthers and filaments are minute and not clearly visible. Pistil: The pistil is minute and not clearly visible.

*Roots*—White fleshy roots with numerous smaller laterals. Roots which develop above the soil surface have a 46A color

*Ultimate size*—The ultimate size of Anthurium '75-10' is unknown as plants continue to enlarge if give proper conditions. However, a 2-year old specimen in a 35-cm container has reached the following dimensions: Canopy height=50 cm; canopy diameter=75–80 cm; leaf length=29–30 cm; leaf width=16–17 cm; spathe length=12–13 cm; spathe width=8 cm and spadix length=5–6 cm.

*Diseases*—No unusual susceptibility to diseases noted to date.

*Insects*—No unusual susceptibility to insects noted to date.

General observations—Anthurium '75-10' is attractive inflorescences composed of red spathes with a red-purple spadix carried on dark red-brown peduncles. The flowers are held slightly above the foliage with the leaves being dark green, shiny and often have light reddish-brown petioles. The plant canopy width is greater than the canopy height and the plant habit is freely branching, compact and upright which make it an attractive and unusual pot plant.

The cultivar may be compared with known varieties along the following lines where observation were made on plants grown under similar conditions near Apopka, Fla.

Anthurium 'Lady Jane' 75-10 has red-brown peduncles that hold the inflorescences higher above the foliage and the spadix is red-purple.

I claim:

1. A new and distinct of Anthurium, substantially as described and illustrated herein, characterized particularly as to novelty by its attractive inflorescences composed of red spathes with a red-purple spadix carried on dark red-brown peduncles, flowers held slightly above the foliage, the leaves being dark green, shiny and often having light reddish-brown petioles, the plant canopy width being greater than the canopy height, and the plant habit being freely branching, compact and upright providing a cultivar well suited as a flowering pot plant having no unusual susceptibility to the traditional Anthurium diseases and insects.

* * * * *